United States Patent [19]
Dines

[11] 3,980,684
[45] Sept. 14, 1976

[54] METALLOCENE INTERCALATES

[75] Inventor: Martin B. Dines, Westfield, N.J.

[73] Assignee: Exxon Research and Engineering Company, Linden, N.J.

[22] Filed: Nov. 26, 1974

[21] Appl. No.: 527,191

[52] U.S. Cl. .................. 260/429 CY; 250/272; 250/475; 260/429.3; 260/429.5; 260/429.7; 260/438.5 R; 260/439 CY

[51] Int. Cl.² .................. C07F 7/00; C07F 7/28; C07F 11/00; C07F 13/00

[58] Field of Search ............... 260/429 CY, 439 CY, 260/429.3, 429.5, 429.7, 438.5 R

[56] References Cited
UNITED STATES PATENTS

| | | | |
|---|---|---|---|
| 3,030,398 | 4/1962 | Shapiro et al. | 260/429 CY |
| 3,673,015 | 6/1972 | Sollatt et al. | 260/439 CY X |
| 3,688,109 | 8/1972 | Gamble | 250/272 |
| 3,711,280 | 1/1973 | Johnson | 260/429 CY X |

OTHER PUBLICATIONS
Advances in Organometallic Chemistry, Academic Press, N.Y., vol. 8, pp. 225, 226, 234, 260, 261 (1970).

*Primary Examiner*—Helen M. S. Sneed
*Attorney, Agent, or Firm*—Joseph J. Allocca

[57] ABSTRACT

A new group of materials is afforded by the intercalation of metallocenes into the layered structure of metal dichalcogenides, said new material being represented by the general formula:

$$TZ_2[M(C_5H_{m-q}X_q)_2]_n$$

where T is a member of Group IVb, Vb, tin, or mixtures thereof, or is a mixture of Group Vb and VIb wherein Vb is at least 50% of the mixture, Z is sulfur, selenium, or mixtures thereof, M is chromium, cobalt, iridium, rhodium or mixtures thereof, $n$ is 0.10 to 0.4, $m$ is 5, $q$ is 0 to 5 and X is an organic radical which is the same or different and is selected from the group consisting of $C_1$–$C_{12}$ linear and branched hydrocarbyls, $C_3$–$C_{12}$ cyclic alkyls, $C_2$–$C_{12}$ alkenyls, $C_2$–$C_{12}$ alkynyls, $C_1$–$C_{12}$ alkoxy, $C_6$–$C_{18}$ aryloxy, $C_6$–$C_{18}$ aryls.

23 Claims, No Drawings

METALLOCENE INTERCALATES

The metallocenes are a relatively new group of organometallic compounds which became recognized after the discovery of di-$\pi$-cyclopentadienyliron, ($\pi$-$C_5H_5$)$_2$ Fe, (ferrocene). The metallocenes are characterized as having a structure such that a metal ion is situated between two five carbon member rings (which display aromaticity as illustrated below:

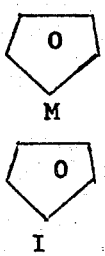
I

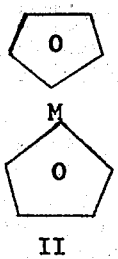
II where M is the metal ion and where the symmetrical five membered rings are either staggered (II) or eclipsed (I) depending upon packing forces and temperature.

Of the metallocenes so far isolated, only ferrocene is air stable, the others being sensitive to oxidation by air, the order of stability, based on ionization potential data, and borne out by experimental observation, being as follows:

TABLE I

| Compound | Ionization Potential |
|---|---|
| $(C_5H_5)_2Co$ | 5.95 eV |
| $(C_5H_5)_2Cr$ | 6.26 eV |
| $(C_5H_5)_2Ti$ | 6.47 eV |
| $(C_5H_5)_2Ni$ | 6.75 eV |
| $(C_5H_5)_2Fe$ | 7.05 eV |
| $(C_5H_5)_2Mn$ | 7.32 eV |
| $(C_5H_5)_2V$ | 7.33 eV |
| $(C_5H_5)_2Mg$ | 7.76 eV |
| $(C_5H_5)_2Ru$ | 7.80 eV |

Metallocenes demonstrate such instability because the metals in the "sandwich" are in a formal zero valence state and, therefore, behave like base metals, easily losing an electron thus exhibiting electropositive characteristics.

The layered chalcogenides are oxidants, that is, they readily accept electrons and, therefore react quite readily with electropositive species such as alkali metals, simultaneously oxidizing them and intercalating them (inserting the metal ion between the layers) to give a product of the form:

$TiS_2 + A \rightarrow A^+TiS_2^-$ (intercalated)

where A is typically an alkali metal.

It has been discovered, and forms the basis of this invention, that at least two of the metallocenes identified in Table I will intercalate into some of the layered metal dichalcogenides. This composition can most easily be described as follows:

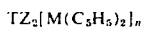
$TZ_2[M(C_5H_5)_2]_n$ more or generally as:

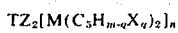
$TZ_2[M(C_5H_{m-q}X_q)_2]_n$ where $TZ_2$ is the layered metal dichalcogenides wherein T is a member of Group IVb or Vb of the Periodic Table of the

| Ti | V |
| Zr | Nb |
| Hf | Ta |

Elements, tin or mixtures thereof, or mixtures of Vb and VIb wherein Group Vb is at least 50% of the mixture, and Z is sulfur, selenium, or mixtures thereof and where $[M(C_5H_{m-q}X_q)_2]_n$ is the intercalated metallocene in which M is chromium, cobalt, iridium, rhodium or mixtures thereof, n is 0.10 to 0.4, m is 5, q goes from 0 to 5 and X is an organic radical which may be the same or different at increasing q value and is selected from the group consisting of $C_1$-$C_{12}$ linear and branched hydrocarbyls, $C_3$-$C_{12}$ cyclic alkyls, $C_2$-$C_{12}$ alkenyls, $C_2$-$C_{12}$ alkynyls, $C_1$-$C_{12}$ alkoxy, $C_6$-$C_{18}$ aryloxy and $C_6$-$C_{18}$ aryls.

Examples of compounds within the scope of the above general formula are:

$TiS_2(Co(C_5H_5)_2)_{0.10-0.40}$
$TiS_2(Cr(C_5H_5)_2)_{0.10-0.40}$
$TiS_2(Ir(C_5H_5)_2)_{0.10-0.40}$
$TiS_2(Rh(C_5H_5)_2)_{0.10-0.40}$
$TiSe_2(Co(C_5H_5)_2)_{0.10-0.40}$
$TiSe_2(Cr(C_5H_5)_2)_{0.10-0.40}$
$TiSe_2(Ir(C_5H_5)_2)_{0.10-0.40}$
$TiSe_2(Rh(C_5H_5)_2)_{0.10-0.40}$
$ZrS_2(Co(C_5H_5)_2)_{0.10-0.40}$
$ZrS_2(Cr(C_5H_5)_2)_{0.10-0.40}$
$ZrS_2(Ir(C_5H_5)_2)_{0.10-0.40}$
$ZrS_2(Rh(C_5H_5)_2)_{0.10-0.40}$
$HfS_2(Co(C_5H_5)_2)_{0.10-0.40}$
$HfS_2(Cr(C_5H_5)_2)_{0.10-0.40}$
$HfS_2(Ir(C_5H_5)_2)_{0.10-0.40}$
$HfS_2(Rh(C_5H_5)_2)_{0.10-0.40}$
$NbSe_2(Co(C_5H_5)_2)_{0.10-0.40}$
$NbSe_2(Cr(C_5H_5)_2)_{0.10-0.40}$
$NbSe_2(Ir(C_5H_5)_2)_{0.10-0.40}$
$NbSe_2(Rh(C_5H_5)_2)_{0.10-0.40}$
$TaS_2(Co(C_5H_5)_2)_{0.10-0.40}$
$TaS_2(Cr(C_5H_5)_2)_{0.10-0.40}$
$TaS_2(Ir(C_5H_5)_2)_{0.10-0.40}$
$TaS_2(Rh(C_5H_5)_2)_{0.10-0.40}$
$TaSe_2(Co(C_5H_5)_2)_{0.10-0.40}$
$TaSe_2(Cr(C_5H_5)_2)_{0.10-0.40}$
$TaSe_2(Ir(C_5H_5)_2)_{0.10-0.40}$
$TaSe_2(Rh(C_5H_5)_2)_{0.10-0.40}$
$SnS_2(Co(C_5H_5)_2)_{0.10-0.40}$

The critical parameter in the preparation of intercalated metallocene dichalcogenides is the ionization potential of the metallocene, that is, the more easily the metallocene loses an electron, the more easily will an intercalation product be formed. It was discovered, and is herein disclosed, that the metallocenes which interact with dichalcogenides to yield an intercalated product are those metallocenes which possess an ionization potential of less than about 6.4 eV.

U.S. Pat. No. 3,688,109 teaches the use of intercalated layered dichalcogenides as x-ray diffraction grating crystals for soft x-rays. The features of the crystal exploited in this use is the large spacing between the dichalcogenide layers. These interlayer spacings for the compounds in the present invention have been measured using the diffraction phenomenon itself. They are given in Table II. Soft x-rays with wavelengths as long as about 20 A can be diffracted with such materials.

EXPERIMENTS

The metallocenes used in the following series of experiments were from commercial sources and were received either as 7.5% solutions in diethylbenzene (used as received) or were dry and subsequently dissolved in a toluene solution to about 5 % by weight.

In a typical preparation, about 250 mg of the layered host $TZ_2$ (prepared by the applicant as needed by conventional techniques) was added to a solution of the metallocene such that the molar ratio was about 1:1. This means that the metallocene was present in about a three to four mole excess. The trials were run at both ambient and elevated temperatures. In the trials run at elevated temperatures (100°–200°C), the reaction was conducted in a sealed glass tube. In the room temperature runs the reaction was conducted in a vial. All reactions were run in an inert atmosphere of helium or nitrogen since the metallocenes are sensitive to oxygen. After 4 days to a week or more, the reaction product was worked up (after cooling) by filtering and washing the product with toluene or benzene in a dry box. The dried products were weighed and the stoichiometry deduced from the weight gain. The results of the various runs can be seen in Table II.

as starting material, indicating that physical intrusion rather than a chemical reaction is occurring.

Runs were also conducted in which it was attempted to form compounds of tantalum disulfide ($TaS_2$) with all of the metallocenes identified in Table III.

TABLE III

| Metallocene | Ionization Potential (eV) |
|---|---|
| Cobaltocene | 5.95 |
| Chromocene | 6.26 |
| Titanocene | 6.47 |
| Nickelocene | 6.75 |
| Ferrocene | 7.05 |
| Manganocene | 7.32 |
| Vanadocene | 7.33 |

It was observed that even when heated to 200°C. either in an aromatic solvent or neat (no solvent) in a sealed tube for a week, metallocenes 3 through 7 formed no product, that is, X-ray powder patterns of the "product" showed only tantalum disulfide starting material. This result is possibly explained as follows: Ionization of the metallocene must occur to form the intercalate and if the energy of ionization is greater than about 6.3–6.4 eV, the reaction will not spontaneously proceed. Thus it is that cobaltocene and chromocene, ionization potential 5.95 and 6.26 eV respectively, form intercalated products and of the two cobaltocene reacts most readily while chromacene requires slightly more rigorous reaction conditions.

TABLE II

| Intercalate | Prep. Cond. | Interlayer Spacing | Lattice Expansion (Δ) | Analysis Calc'd (for °25) | | Found | |
|---|---|---|---|---|---|---|---|
| | | | | T | M | T | M |
| $TiS_2(Co(C_5H_5)_2)_{0.20}$ | 23°C. | 11.25 A | 5.55 A | 30.1 | 9.3 | 30.5 | 9.6 |
| $TiS_2(Cr(C_5H_5)_2)_{0.30}$ | 100°C. | 11.16 A | 5.46 A | 30.4 | 8.3 | 26.5 | 9.5 |
| $TiSe_2(Co(C_5H_5)_2)_{0.38}$ | 23°C. | 11.52 A | 5.52 A | | | | |
| $ZrS_2(Co(C_5H_5)_2)_{0.27}$ | 100°C. | 11.16 A | 5.35 A | | | | |
| $HfS_2(Co(C_5H_5)_2)_{0.38}$ | 100°C. | 11.32 A | 5.48 A | | | | |
| $HfS_2(Cr(C_5H_5)_2)_{0.20}$ | 100°C. | 11.50 A | 5.66 A | | | | |
| $NbSe_2(Co(C_5H_5)_2)_{0.31}$ | 23°C. | 11.83 A | 5.56 A | 31.1 | 4.9 | 25.4 | 5.2 |
| $NbSe_2(Cr(C_5H_5)_2)_{0.20}$ | 100°C. | 11.78 A | 5.51 A | | | | |
| $TaS_2(CO(C_5H_5)_2)_{0.23}$ | 23°C. | 11.52 A | 5.47 A | 61.9 | 5.05 | 60.6 | 5.02 |
| $TaS_2(Cr(C_5H_5)_2)_{0.28}$ | 100°C. | 11.58 A | 5.53 A | 62.3 | 4.5 | 63.2 | 4.3 |
| $TaSe_2(Co(C_5H_5)_2)_{0.30}$ | 23°C. | 11.84 A | 5.49 A | | | | |
| $TaSe_2(Cr(C_5H_5)_2)_{0.29}$ | 200°C. | 11.88 A | 5.53 A | | | | |
| $SnS_2(Co(C_5H_5)_2)_{0.29}$ | 100°C. | 11.22 A | 5.33 A | | | | |

In a few cases (see Table II) the weight gain, as indicated by the fractional subscript, was somewhat excessive and observation under a microscope revealed that some solid was occluded by the product. It is believed that this material is a decomposition product of the metallocene which is strongly adsorbed by the intercalated hosts and which cannot be washed away. However, in all cases cited, the formation of an intercalated adduct of stoichiometry of about 1:4 (metallocene to $TZ_2$) was proven by the X-ray powder diffractograms of the product. These all showed an expansion in the c direction of the lattice (interplanar parallel distance) by 5.5 ± 0.15 A, the value expected for an inclusion compound having the metallocene situated with its long axis parallel to the $TZ_2$ host layered sheets. Although the likely favored stoichiometry is 1:4 (0.25) some variation was observed (0.15–0.4) due to difficulty in removing all unreacted metallocene from the product. This is due to either strong adsorption on the surface or partial decomposition and surface adsorption or occlusion. Analysis reveals, however, that the intercalated species is empirically of the same formula

EXAMPLE: (NMR)

A solid state nmr analysis of the proton second moments and limeshape in $TaS_2(Co(C_5H_5)_2)_{0.25}$ was performed.

The room temperature line has a width of 1.5 Gauss broadening to 2.12 Gauss at 100°K. Calculations of the second moments for the 100° and 300°K. traces yields $M_2$=0.793 $G^2$ and 0.46 $G^2$ respectively.

Detailed analysis of the data are consistent with the formulated stoichiometry of ¼ metallocene per $TaS_2$ unit. The data also indicate considerable motional freedom of the intercalated guest species. They are spinning and rotating at room temperature.

EXAMPLE: (TGA)

Using a Dupont 900 thermogravimetric analyzer, an experiment was performed in which $TaS_2(Co(C_5H_5)_2)_{0.25}$ in an inert atmosphere was gradually heated to about 450°C. No weight loss was seen in this run showing the thermal stability toward deintercalation of the guest.

EXAMPLE

The following table summarizes the results of measurements of the superconductive behavior and the magnetic properties of several of the products. The experiments were conducted using a vibrating magnetometer at liquid helium temperatures.

| Material | Superconductive Behavior | Magnetic Properties |
|---|---|---|
| $TiS_2(Co(C_5H_5)_2)_{0.20}$ | None | Pauli-paramagnetic |
| $TiS_2(Cr(C_5H_5)_2)_{0.3}$ | None | Paramagnetic; $\mu_{eff}=$ 3.15 BM |
| $HfS_2(Co(C_5H_5)_2)_{0.38}$ | None | Pauli-paramagnetic |
| $NbSe_2(Co(C_5H_5)_2)_{0.3}$ | Questionable | Pauli-paramagnetic |
| $NbSe_2(Cr(C_5H_5)_2)_{0.20}$ | $Tc = 4.5°K.$ | Paramagnetic; $\mu_{eff}=$ 3.23 BM |
| $TaS_2(Co(C_5H_5)_2)_{0.23}$ | $Tc = 3.2°K.$ | Pauli-paramagnetic |
| $TaS_2(Cr(C_5H_5)_2)_{0.28}$ | $Tc = 2.9°K.$ | Paramagnetic; $\mu_{eff}=$ 3.1 BM |

The last three samples were found to be superconducting.

What is claimed is:

1. A composition of matter of the formula $$TZ_2[M(C_5H_{m-q}X_q)_2]_n$$

in which $TZ_2$ is a layered metal dichalcogenide in which T is a member of Group IVb, Vb, Sn or mixtures thereof, or is a mixture of Group Vb and VIb wherein Vb is at least 50% of the mixture, and Z is sulfur, selenium or mixtures thereof and in which $[M(C_5H_{m-q}X_q)_2]_n$ is the intercalated metallocene in which M is cobalt, chromium, iridium, rhodium or mixtures thereof, n is 0.10 to 0.40, m is 5, q is 0 to 5 and X is an organic radical which may be the same or different and is selected from the group consisting of $C_1$–$C_{12}$ linear and branched hydrocarbyls, $C_1$–$C_{12}$ alkoxy and $C_6$–$C_{18}$ aryloxy.

2. A composition of matter according to claim 1 wherein T is Ti, Z is sulfur, M is Co or Cr, m is 5, q is 0 and n is 0.10 to 0.40.

3. A composition of matter according to claim 1 wherein T is Ti, Z is selenium, M is Co or Cr, m is 5, q is 0 and n is 0.10 to 0.40.

4. A composition of matter according to claim 1 wherein T is Nb, Z is selenium, M is Co or Cr, m is 5, q is 0 and n is 0.10 to 0.40.

5. A composition of matter according to claim 1 wherein T is Ta, Z is sulfur, M is Co or Cr, m is 5, q is 0 and n is 0.10 to 0.40.

6. A composition of matter according to claim 1 wherein T is Ta, Z is selenium, M is Co or Cr, m is 5, q is 0 and n is 0.10 to 0.40.

7. A composition of matter according to claim 1 wherein T is Hf, Z is sulfur, M is Co or Cr, m is 5, q is 0 and n is 0.10 to 0.40.

8. A composition of matter according to claim 1 wherein T is Zr, Z is sulfur, M is Co or Cr, m is 5, q is 0 and n is 0.10 to 0.40.

9. A composition of matter according to claim 1 wherein T is Tin, Z is sulfur, M is Co, m is 5, q is 0 and n is 0.10 to 0.40.

10. A composition of matter according to claim 1 of the formula $TiS_2(Co(C_5H_5)_2)_{0.20}$.

11. A composition of matter according to claim 1 of the formula $TiS_2(Cr(C_5H_5)_2)_{0.30}$.

12. A composition of matter according to claim 1 of the formula $TiSe_2(Co(C_5H_5)_2)_{0.38}$.

13. A composition of matter according to claim 1 of the formula $ZrS_2(Co(C_5H_5)_2)_{0.27}$.

14. A composition of matter according to claim 1 of the formula $HfS_2(Co(C_5H_5)_2)_{0.38}$.

15. A composition of matter according to claim 1 of the formula $HfS_2(Cr(C_5H_5)_2)_{0.20}$.

16. A composition of matter according to claim 1 of the formula $NbSe_2(Co(C_5H_5)_2)_{0.31}$.

17. A composition of matter according to claim 1 of the formula $NbSe_2(Cr(C_5H_5)_2)_{0.20}$.

18. A composition of matter according to claim 1 of the formula $TaS_2(Co(C_5H_5)_2)_{0.23}$.

19. A composition of matter according to claim 1 of the formula $TaS_2(Cr(C_5H_5)_2)_{0.28}$.

20. A composition of matter according to claim 1 of the formula $TaSe_2(Co(C_5H_5)_2)_{0.30}$.

21. A composition according to claim 1 of the formula $TaSe_2(Cr(C_5H_5)_2)_{0.29}$.

22. A composition of matter according to claim 1 of the formula $SnS_2(Co(C_5H_5)_2)_{0.29}$.

23. A composition of matter according to claim 1 wherein m is 5, q is 0 and n is 0.10 to 0.40.

* * * * *